(12) United States Patent
Duindam et al.

(10) Patent No.: US 11,622,669 B2
(45) Date of Patent: Apr. 11, 2023

(54) SYSTEMS AND METHODS OF REGISTRATION FOR IMAGE GUIDED SURGERY

(71) Applicant: Intuitive Surgical Operations, Inc., Sunnyvale, CA (US)

(72) Inventors: Vincent Duindam, San Francisco, CA (US); Federico Barbagli, San Francisco, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/412,705

(22) Filed: Aug. 26, 2021

(65) Prior Publication Data

US 2021/0386487 A1     Dec. 16, 2021

Related U.S. Application Data

(63) Continuation of application No. 15/574,545, filed as application No. PCT/US2016/033596 on May 20, 2016, now Pat. No. 11,116,581.

(Continued)

(51) Int. Cl.
*A61B 34/20*     (2016.01)
*A61B 1/00*     (2006.01)
(Continued)

(52) U.S. Cl.
CPC ............ *A61B 1/0005* (2013.01); *A61B 1/005* (2013.01); *A61B 1/009* (2022.02); *A61B 1/05* (2013.01);
(Continued)

(58) Field of Classification Search
CPC ....... A61B 34/20; A61B 1/005; A61B 1/0005; A61B 5/06; A61B 34/25; A61B 34/35;
(Continued)

(56) References Cited

U.S. PATENT DOCUMENTS 6,380,732 B1   4/2002   Gilboa
6,389,187 B1   5/2002   Greenaway et al.
(Continued)

FOREIGN PATENT DOCUMENTS

CN     103648361 A     3/2014
JP     2009279250 A    12/2009
(Continued)

OTHER PUBLICATIONS

International Preliminary Report on Patentability for Application No. PCT/US2016/033596, dated Dec. 7, 2017, 7 pages.
(Continued)

*Primary Examiner* — Bo Joseph Peng
(74) *Attorney, Agent, or Firm* — Haynes and Boone, LLP

(57) ABSTRACT

A system includes a manipulator and a processing unit. The processing unit is configured to receive, from a position sensor system, a collected set of spatial information for a distal portion of a medical instrument collected at locations within anatomic passageways as a rigid instrument body is moved in an insertion or retraction direction. The processing unit is further configured to receive, from a position measuring device, a set of position information related to a position of the rigid instrument body when the distal portion is at the locations. The processing unit is further configured to, based at least in part on the set of position information, determine a subset of the set of spatial information relative to the environment coordinate space and, based on the subset of spatial information, determine an initial transform for (Continued)

registering the set of spatial information with anatomical model information in a model coordinate space.

20 Claims, 11 Drawing Sheets

Related U.S. Application Data

(60) Provisional application No. 62/165,249, filed on May 22, 2015.

(51) Int. Cl.

| | | |
|---|---|---|
| *A61B 1/267* | (2006.01) | |
| *G06T 19/00* | (2011.01) | |
| *A61B 1/005* | (2006.01) | |
| *G06T 19/20* | (2011.01) | |
| *G06T 7/33* | (2017.01) | |
| *A61B 5/06* | (2006.01) | |
| *A61B 34/00* | (2016.01) | |
| *A61B 34/35* | (2016.01) | |
| *A61B 34/37* | (2016.01) | |
| *G06T 7/10* | (2017.01) | |
| *A61B 1/05* | (2006.01) | |
| *A61B 10/04* | (2006.01) | |

(52) U.S. Cl.
CPC .............. *A61B 1/2676* (2013.01); *A61B 5/06* (2013.01); *A61B 10/04* (2013.01); *A61B 34/20* (2016.02); *A61B 34/25* (2016.02); *A61B 34/35* (2016.02); *A61B 34/37* (2016.02); *G06T 7/10* (2017.01); *G06T 7/33* (2017.01); *G06T 7/337* (2017.01); *G06T 7/344* (2017.01); *G06T 19/00* (2013.01); *G06T 19/006* (2013.01); *G06T 19/20* (2013.01); *A61B 2034/2051* (2016.02); *A61B 2034/2061* (2016.02); *G06T 2207/10068* (2013.01); *G06T 2207/30061* (2013.01)

(58) Field of Classification Search
CPC ........... A61B 34/37; A61B 1/05; A61B 10/04; A61B 1/2676; A61B 2034/2051; A61B 2034/2061; A61B 1/009; A61B 2017/00809; A61B 5/0084; A61B 1/00009; A61B 1/00055; A61B 1/0051; A61B 5/02007; A61B 5/02028; A61B 5/6852; G06T 7/337; G06T 19/00; G06T 19/20; G06T 7/33; G06T 7/10; G06T 7/344; G06T 19/006; G06T 2207/10068; G06T 2207/30061; G06T 19/003

See application file for complete search history.

(56) References Cited

U.S. PATENT DOCUMENTS

| | | |
|---|---|---|
| 7,316,681 B2 | 1/2008 | Madhani et al. |
| 7,772,541 B2 | 8/2010 | Froggatt et al. |
| 8,900,131 B2 | 12/2014 | Chopra et al. |
| 9,259,274 B2 | 2/2016 | Prisco |
| 9,452,276 B2 | 9/2016 | Duindam et al. |
| 11,116,581 B2 | 9/2021 | Duindam et al. |
| 2004/0097806 A1 | 5/2004 | Hunter et al. |
| 2005/0182295 A1 | 8/2005 | Soper et al. |
| 2006/0013523 A1 | 1/2006 | Childlers et al. |
| 2008/0119727 A1 | 5/2008 | Barbagli et al. |
| 2010/0125285 A1 | 5/2010 | Sewell et al. |
| 2010/0249506 A1 | 9/2010 | Prisco |
| 2011/0319910 A1 | 12/2011 | Roelle et al. |
| 2012/0065481 A1 | 3/2012 | Hunter et al. |
| 2013/0223702 A1 | 8/2013 | Holsing et al. |
| 2013/0303893 A1 | 11/2013 | Duindam et al. |
| 2014/0180087 A1 | 6/2014 | Millett et al. |
| 2014/0275986 A1 | 9/2014 | Vertikov |
| 2014/0275997 A1 | 9/2014 | Chopra et al. |
| 2014/0343416 A1 | 11/2014 | Panescu et al. |
| 2017/0265953 A1 | 9/2017 | Fenech et al. |

FOREIGN PATENT DOCUMENTS

| | | |
|---|---|---|
| WO | WO-2009135070 A1 | 11/2009 |
| WO | WO-2012158324 A2 | 11/2012 |
| WO | WO-2013173229 A1 | 11/2013 |
| WO | WO-2015017270 A1 | 2/2015 |

OTHER PUBLICATIONS

International Search Report and Written Opinion for Application No. PCT/US16/33596, dated Aug. 30, 2016, 10 pages.

Office Action dated Mar. 27, 2020 for Chinese Application No. 201680029022.8 filed on May 20, 2016, 39 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SYSTEMS AND METHODS OF REGISTRATION FOR IMAGE GUIDED SURGERY

RELATED APPLICATIONS

This patent application is a continuation of U.S. patent application Ser. No. 15/574,545, filed Nov. 16, 2017, which is the U.S. national phase of International Application No. PCT/US2016/033596, filed May 20, 2016, which designated the U.S. and claims priority to and the benefit of the filing date of U.S. Provisional Patent Application No. 62/165,249, entitled "SYSTEMS AND METHODS OF REGISTRATION FOR IMAGE GUIDED SURGERY," filed May 22, 2015, both of which are incorporated by reference herein in their entireties.

FIELD

The present disclosure is directed to systems and methods for conducting an image guided procedure, and more particularly to systems and methods for displaying pathology data for tissue sampled during an image guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomical systems such as the lungs, the colon, the intestines, the kidneys, the heart, the circulatory system, or the like. Traditional instrument tracking systems, including electromagnetic sensing tracking systems, may disturb the clinical environment or workflow. Systems and methods for performing image guided surgery with minimal clinical disturbances are needed.

SUMMARY

The embodiments of the invention are summarized by the claims that follow the description.

In one embodiment, a method performed by a computing system comprises receiving a collected set of spatial information for a distal portion of an instrument at a plurality of locations within a set of anatomic passageways and receiving a set of position information for a reference portion of the instrument when the distal portion of the instrument is at each of the plurality of locations. The method also comprises determining a reference set of spatial information for the distal portion of the instrument based on the collected set of spatial information and the set of position information for the reference portion of the instrument and registering the reference set of spatial information with a set of anatomical model information.

In another embodiment, a method comprises collecting a set of spatial information from an optical fiber shape sensor extending within a medical instrument coupled to a teleoperational assembly when a distal portion of the instrument is at a plurality of locations within a set of anatomic passageways. The method also comprises receiving a set of position information from a position sensor for a drive system of the teleoperational assembly when the distal portion of the instrument is at the plurality of locations within the set of anatomic passageways and determining a set of proximal position data for a proximal portion of the instrument when the distal portion of the instrument is at the plurality of locations. The set of proximal position data is determined based upon the position information from the position sensor and calibration information between the position sensor and a fixed insertion track along which the proximal portion of the instrument moves. The method also comprises determining a reference set of spatial information for the distal portion of the instrument based on the collected set of spatial information and the set of proximal position data and registering the reference set of spatial information with a set of anatomical model information.

In another embodiment, a system comprises a teleoperational assembly including an operator control system and a manipulator configured for teleoperation by the operator control system. The manipulator is configured to control movement of a medical instrument in a surgical environment. The system also comprises a processing unit including one or more processors. The processing unit is configured to receive a collected set of spatial information for a distal portion of the medical instrument at a plurality of locations within a set of anatomic passageways and receive a set of position information for a reference portion of the medical instrument when the distal portion of the instrument is at each of the plurality of locations. The processing unit is also configured to determine a reference set of spatial information for the distal portion of the medical instrument based on the collected set of spatial information and the set of position information for the reference portion of the medical instrument and register the reference set of spatial information with a set of anatomical model information.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 5A:
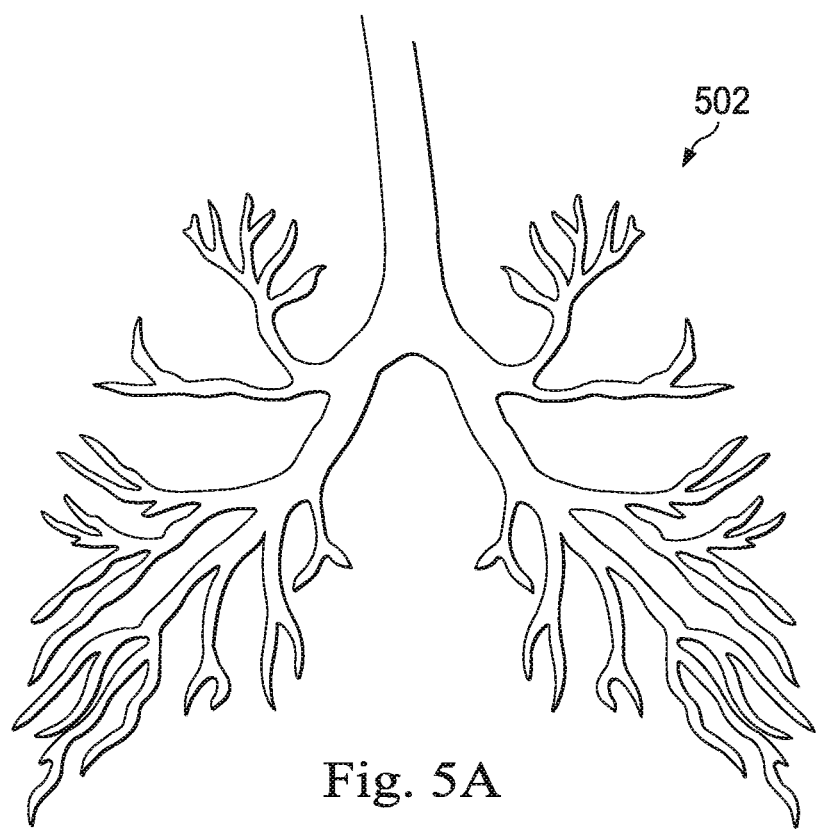
Figure 5B:
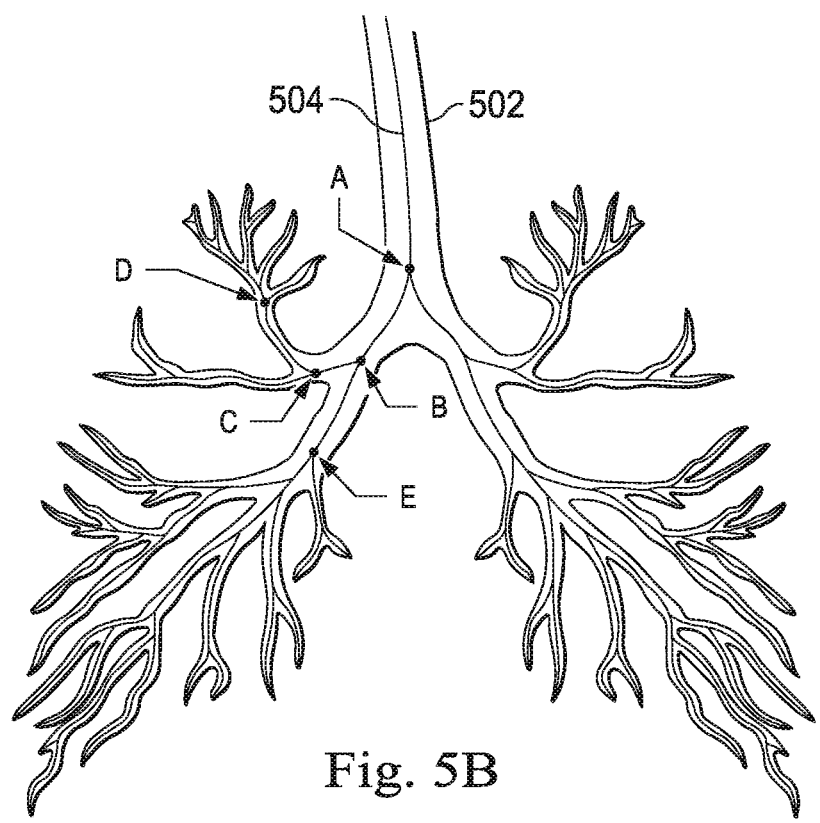
Figure 5C:
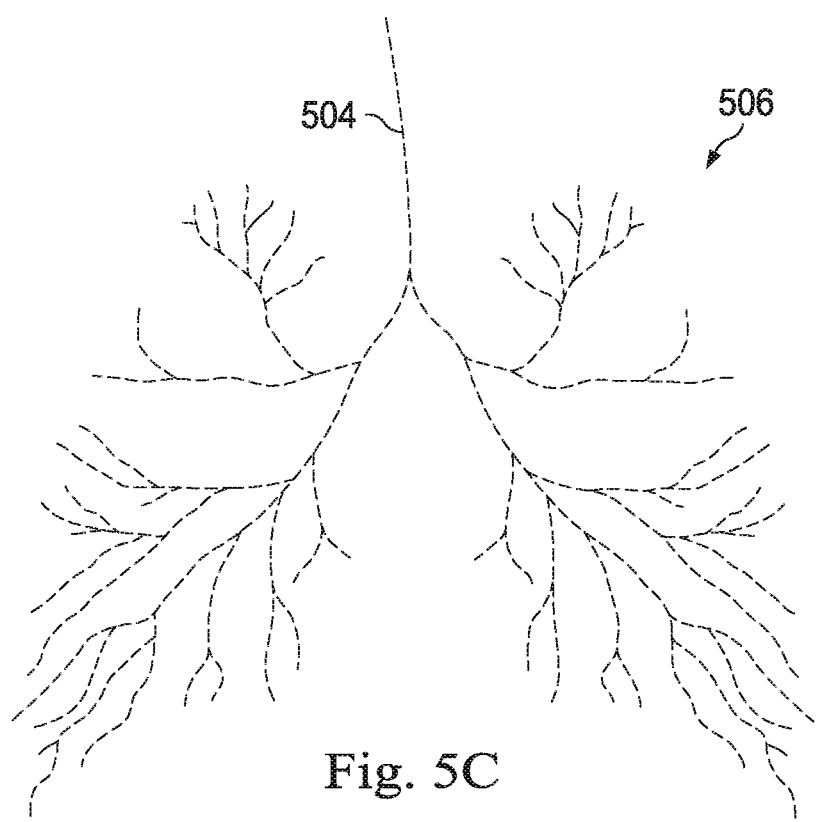

FIGS. 5A, 5B, and 5C illustrate steps in a segmentation process that generates a model of a patient anatomy for registration according to an embodiment of the present disclosure.

Figure 6:
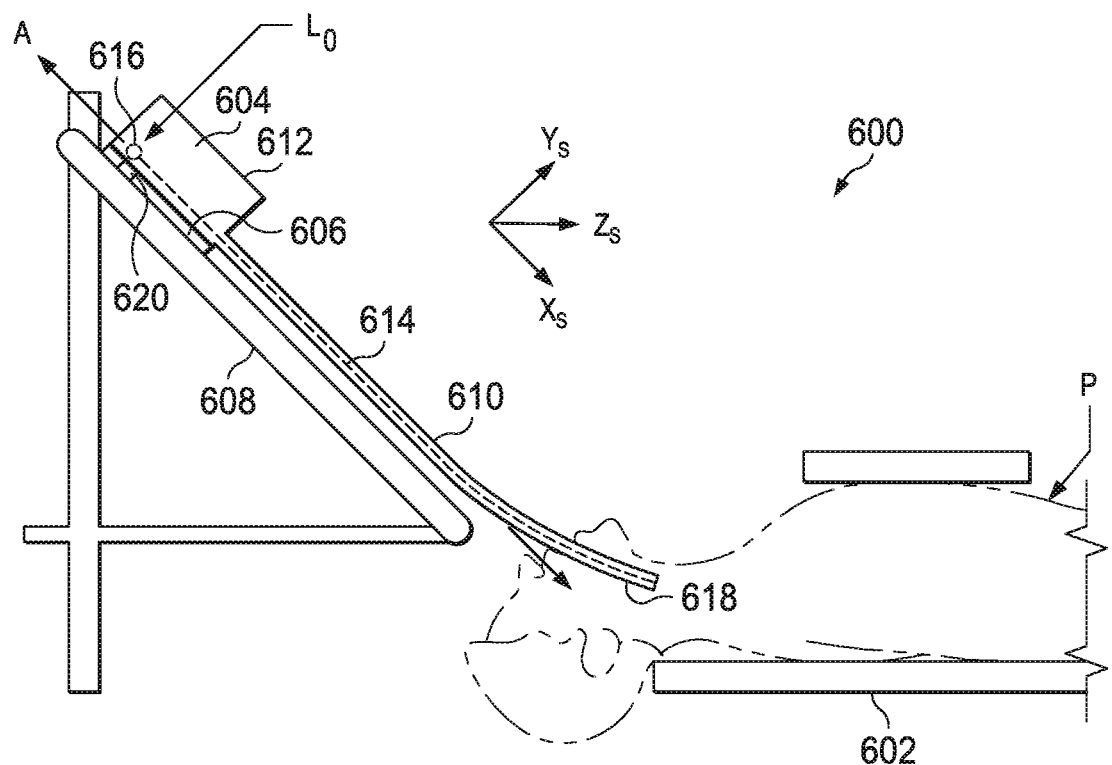
Figure 7:
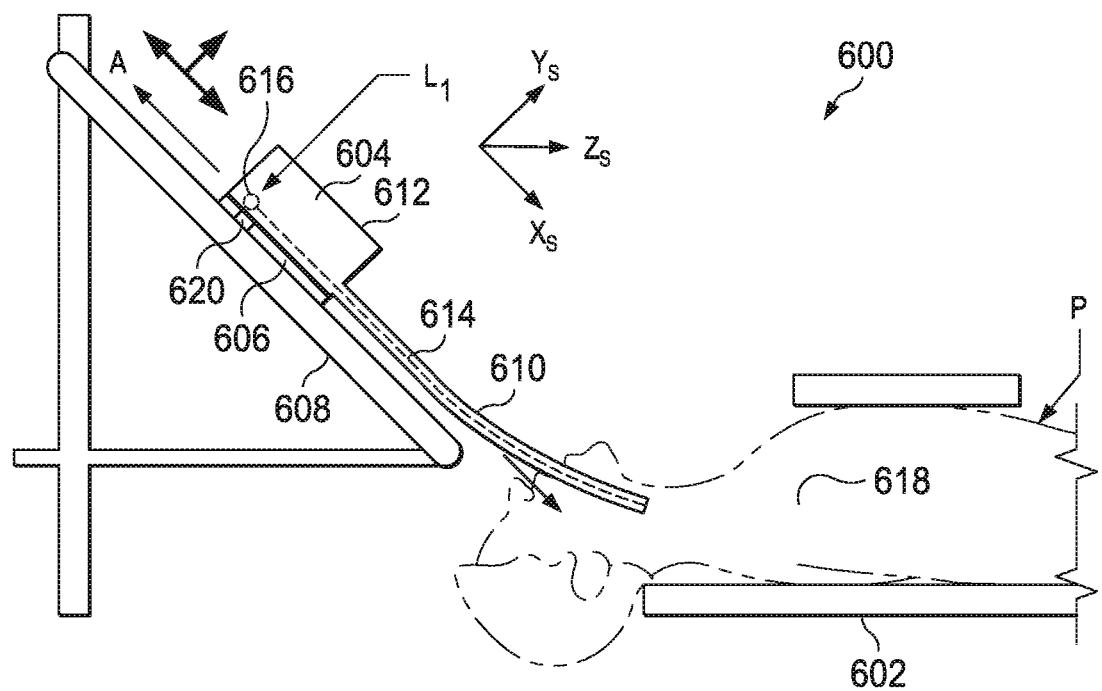

FIGS. 6 and 7 are side views of a surgical coordinate space including a medical instrument mounted on an insertion assembly.

Figure 8:
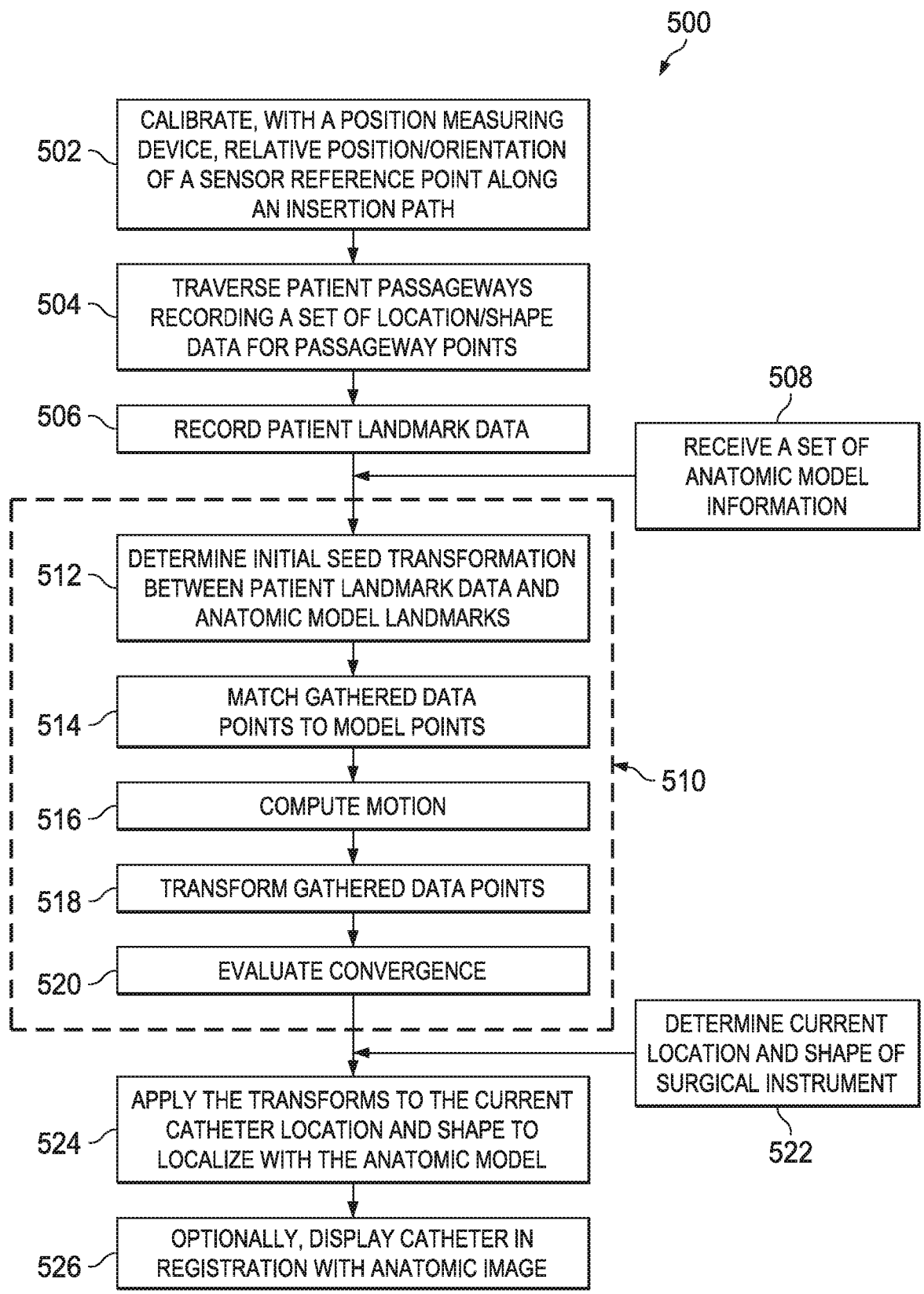

FIG. 8 illustrates flowchart illustration a portion of an image guided surgical procedure according to an embodiment of the present disclosure.

Figure 9:
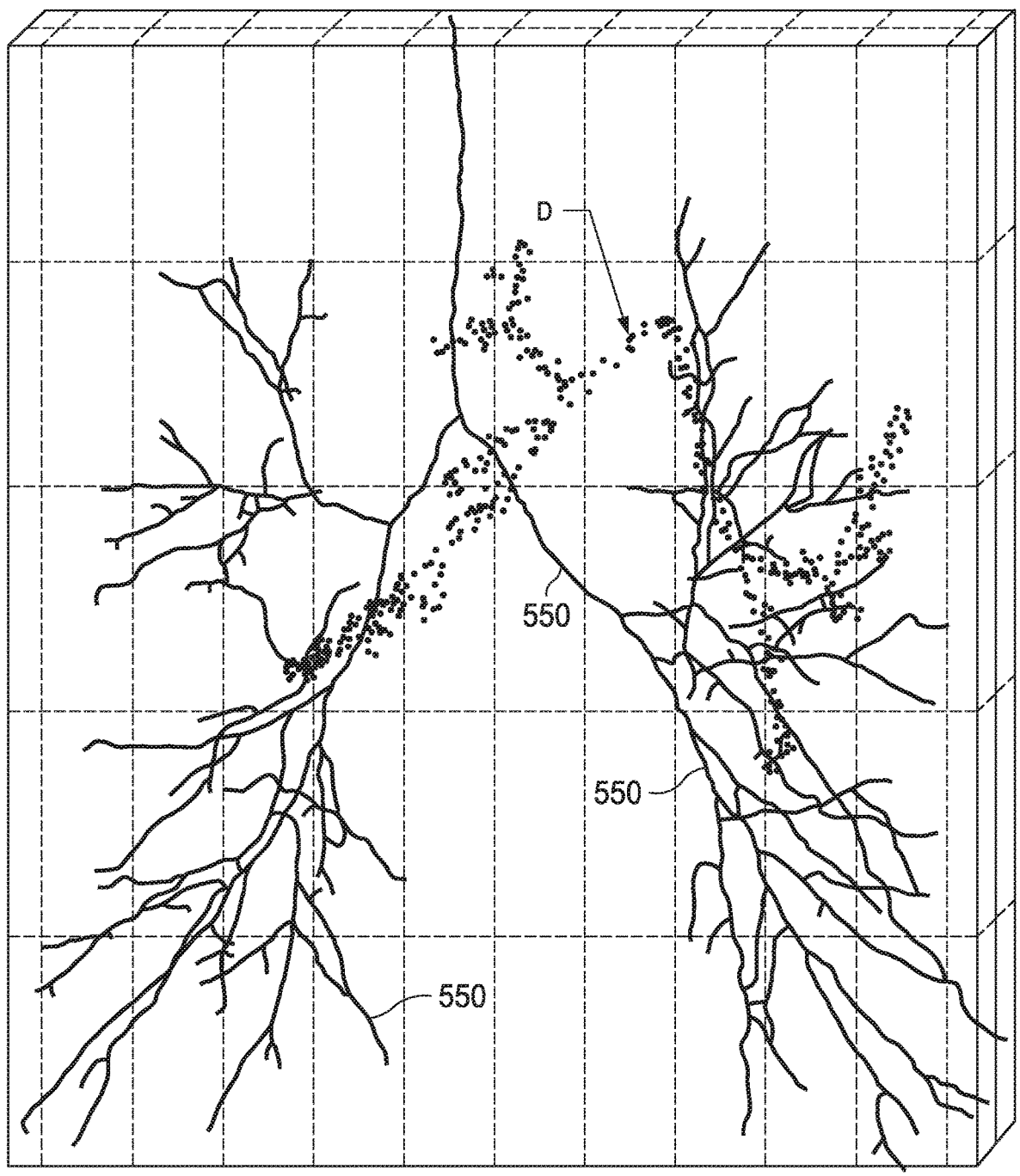
Figure 10:
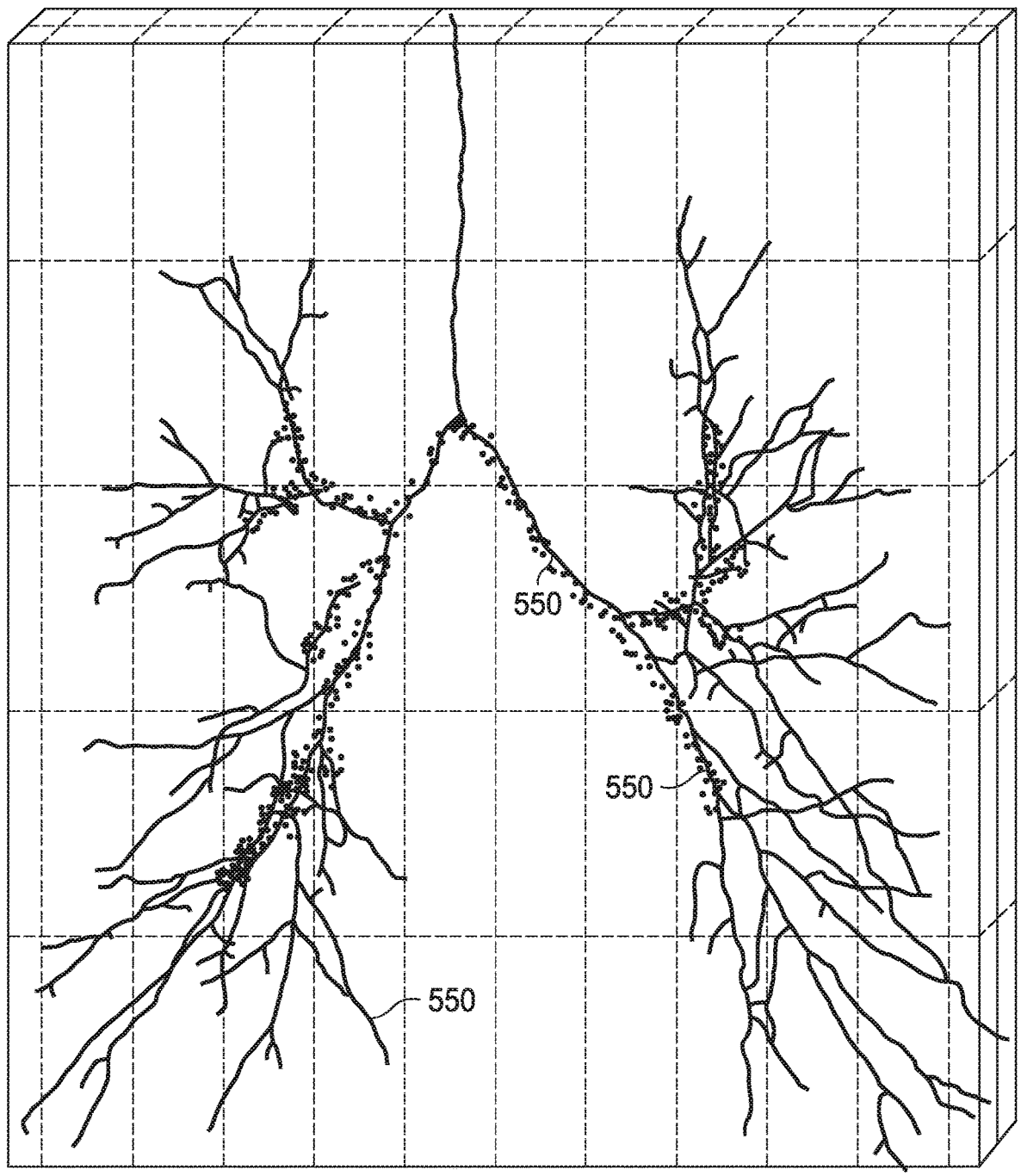

FIGS. 9 and 10 illustrate a registration technique according to an embodiment of the present disclosure.

Figure 11:
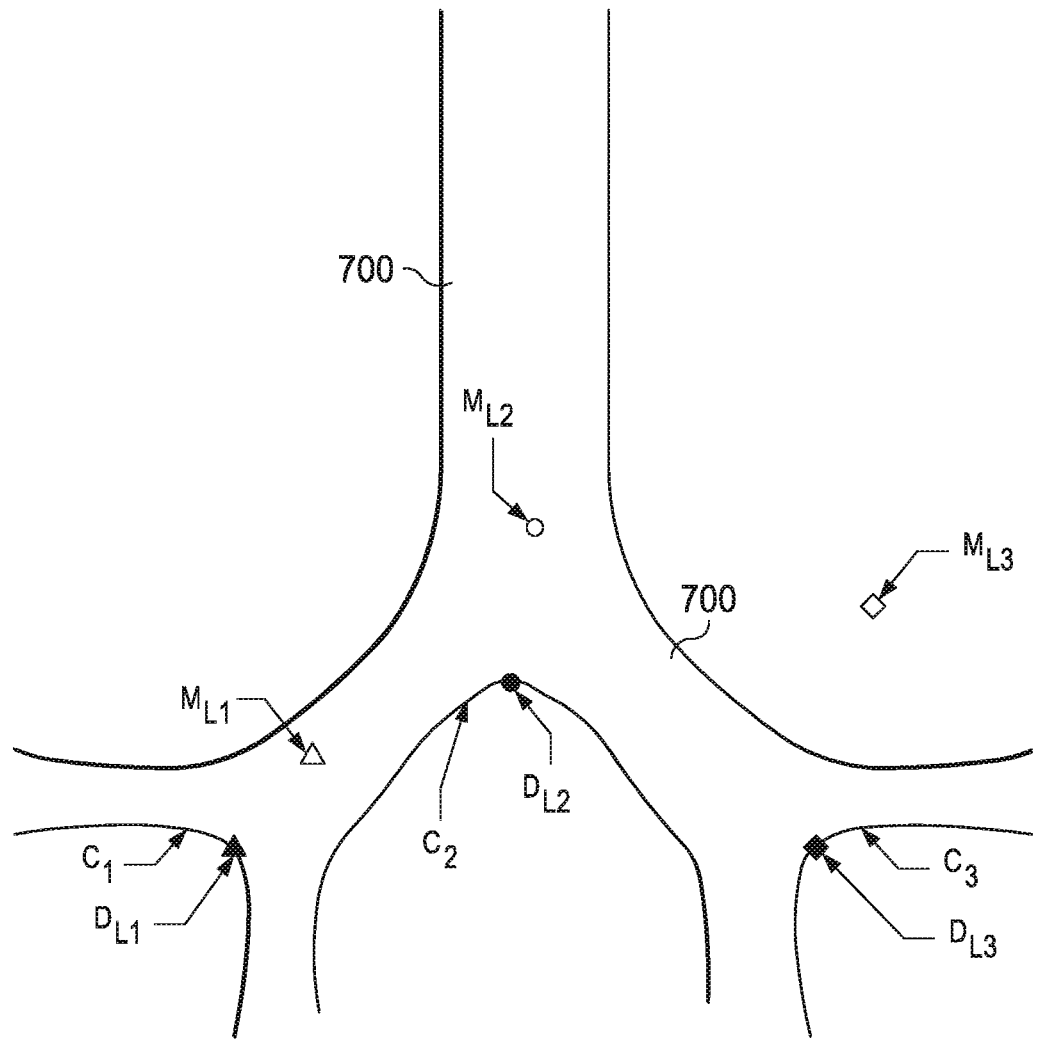

FIG. 11 illustrates a seeding process of an image guided surgical procedure according to an embodiment of the present disclosure.

Figure 12:
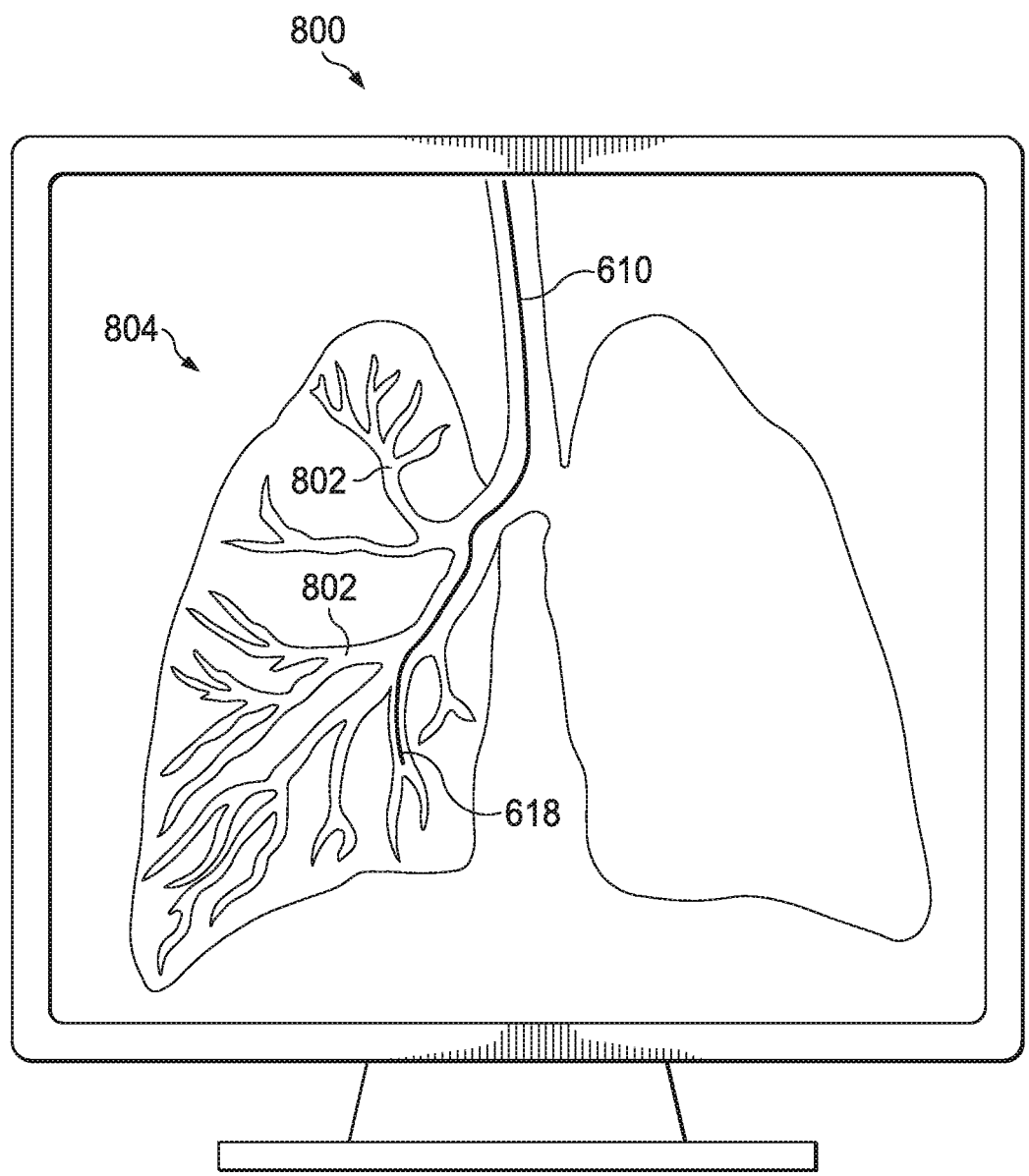

FIG. 12 illustrates a registration display stage of a registration technique according to an embodiment of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
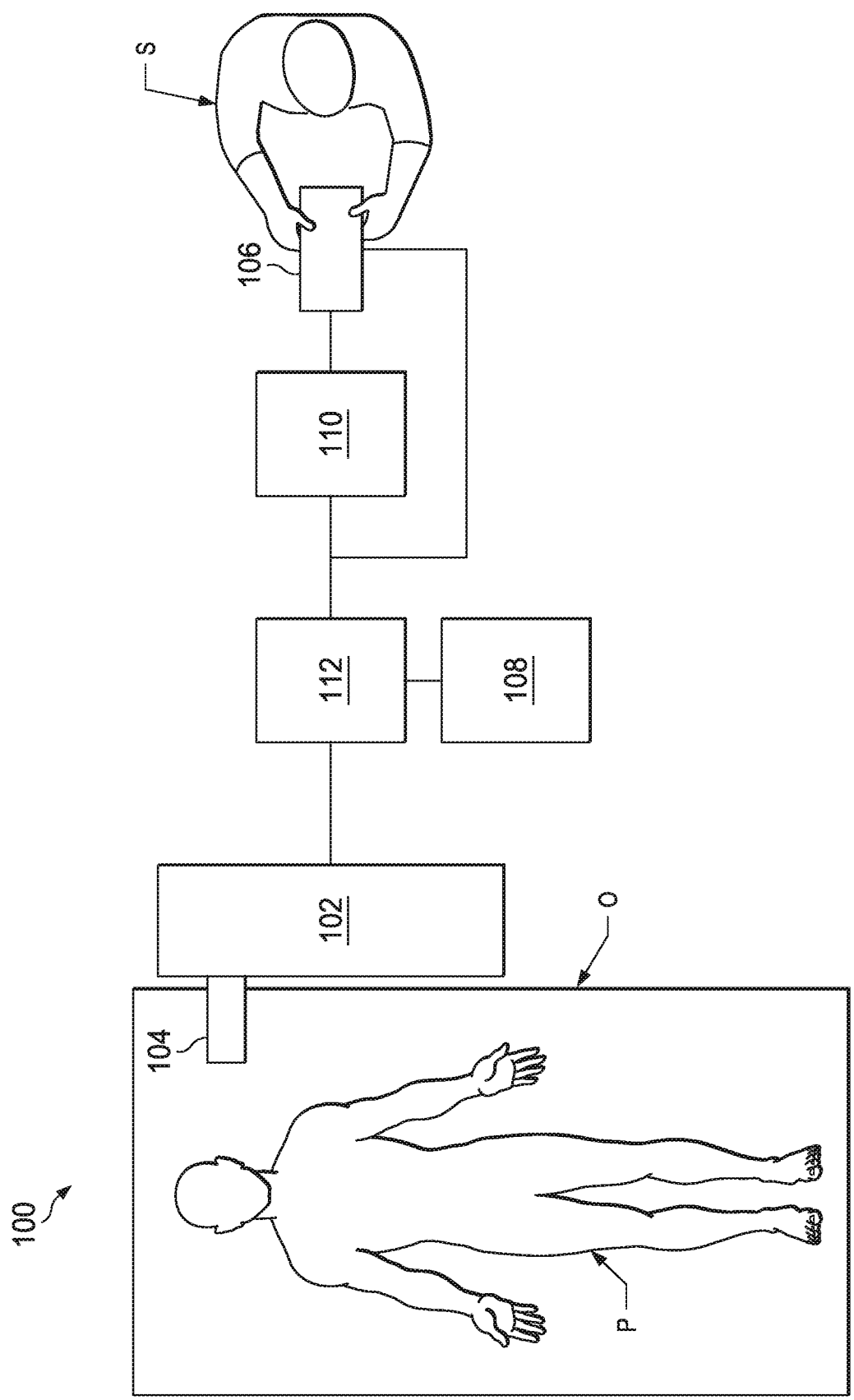
FIG. 1 is a teleoperated medical system, in accordance with embodiments of the present disclosure.

Referring to FIG. 1 of the drawings, a teleoperated medical system for use in, for example, surgical, diagnostic, therapeutic, or biopsy procedures, is generally indicated by the reference numeral 100. As shown in FIG. 1, the teleoperated system 100 generally includes a teleoperational manipulator assembly 102 for operating a medical instrument 104 in performing various procedures on the patient P. The assembly 102 is mounted to or near an operating table O. A master assembly 106 allows the clinician or surgeon S to view the interventional site and to control the slave manipulator assembly 102.

The master assembly 106 may be located at a surgeon's console which is usually located in the same room as operating table O. However, it should be understood that the surgeon S can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated medical instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions corresponding to processes disclosed herein.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011)(disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2A:
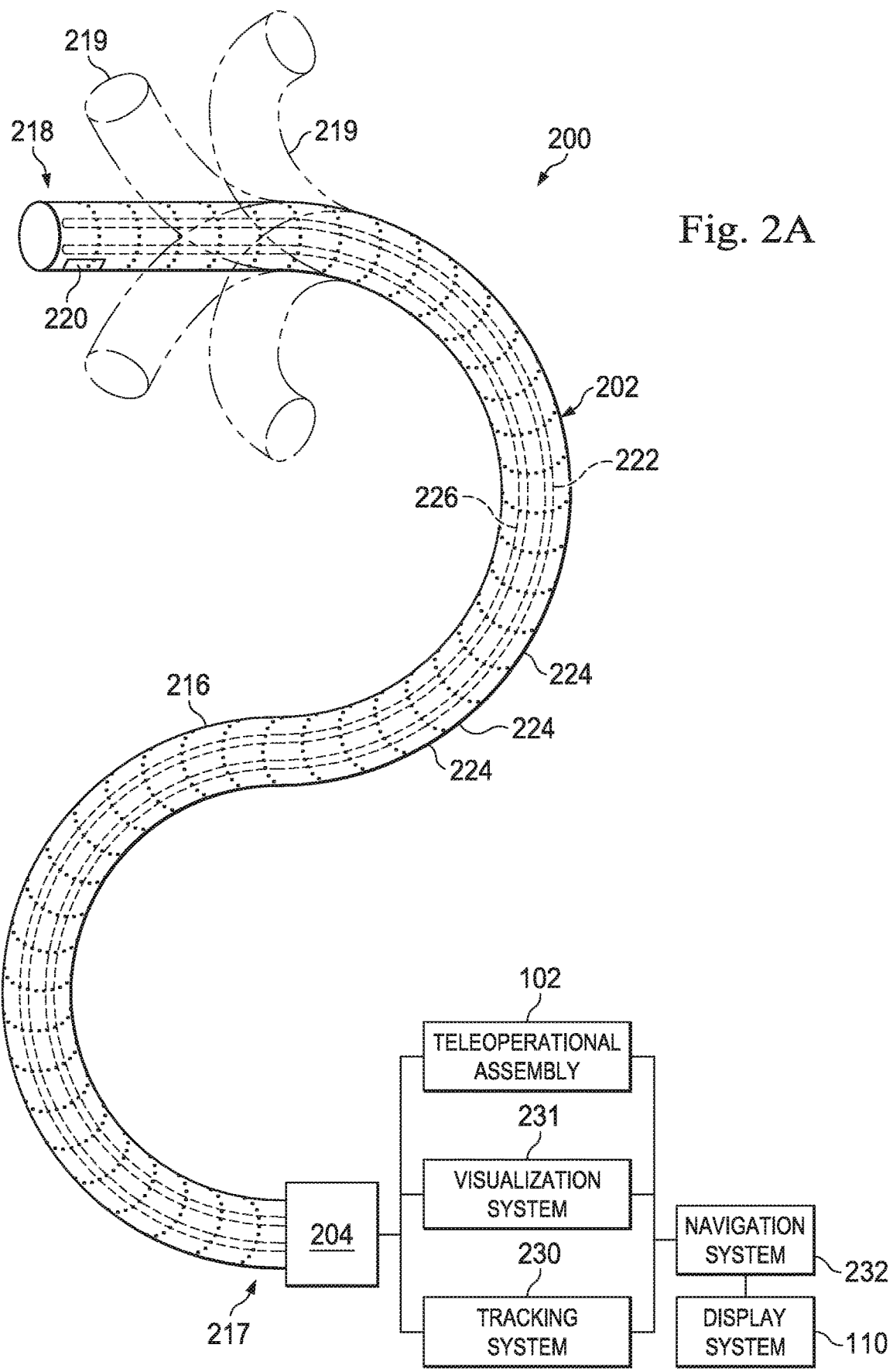
FIG. 2A illustrates a medical instrument system utilizing aspects of the present disclosure.

FIG. 2A illustrates a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an electromagnetic (EM) sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom. e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of the control system 112.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the medical tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 112 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing. "Medical System Providing Dynamic Registration of a Model of an Anatomical Structure for Image-Guided Surgery." which is incorporated by reference herein in its entirety.

In the embodiment of FIG. 2A, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figure 2B:
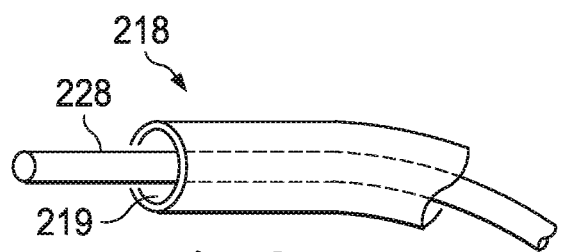
FIG. 2B illustrates a distal end of the medical instrument system of FIG. 2 with an extended medical tool.

As shown in greater detail in FIG. 2B, medical tool(s) 228 for such procedures as surgery, biopsy, ablation, illumination, irrigation, or suction can be deployed through the channel 221 of the flexible body 216 and used at a target location within the anatomy. If, for example, the tool 228 is a biopsy instrument, it may be used to remove sample tissue or a sampling of cells from a target anatomical location. The medical tool 228 may be used with an image capture probe also within the flexible body 216. Alternatively, the tool 228 may itself be the image capture probe. The tool 228 may be advanced from the opening of the channel 221 to perform the procedure and then retracted back into the channel when the procedure is complete. The medical tool 228 may be removed from the proximal end 217 of the catheter flexible body or from another optional instrument port (not shown) along the flexible body.

Figure 4:
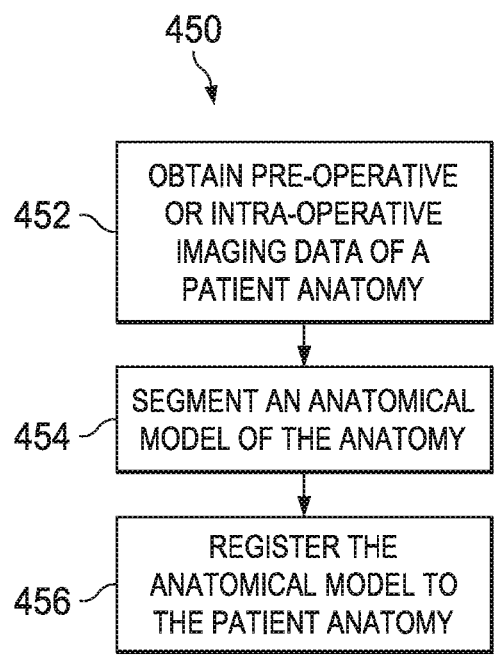
FIG. 4 is a flowchart illustrating a method used to provide guidance in an image guided surgical procedure according to an embodiment of the present disclosure.

FIG. 4 illustrates the catheter system 202 positioned within an anatomic passageway of a patient anatomy. In this embodiment, the anatomic passageway is an airway of a human lung. In alternative embodiments, the catheter system 202 may be used in other passageways of an anatomy.

Figure 3:
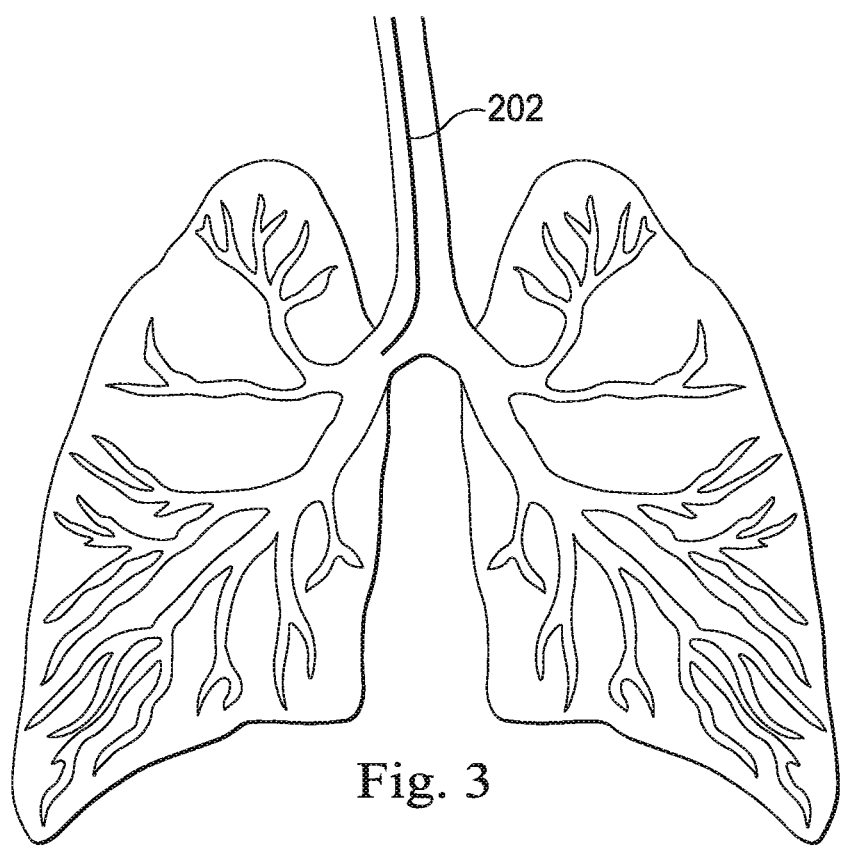
FIG. 3 illustrates the distal end of the medical instrument system of FIG. 2 positioned within a human lung.

FIG. 4 is a flowchart illustrating a general method 450 for use in an image guided surgical procedure. At a process 452, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs 201 of FIG. 3. At a process 454, computer software alone or in combination with manual input is used to convert the recorded images into a segmented two dimensional or three dimensional composite representation or model of a partial or an entire anatomical organ or anatomical region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically. At a process 456, the anatomic model data is registered to the patient anatomy prior to and/or during the course of an image-guided surgical procedure on the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique described in detail at FIG. 6 and elsewhere in this disclosure. Other point set registration methods may also be used in registration processes within the scope of this disclosure.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below perform registration based upon ICP, or another point set registration algorithm, and the calibrated movement of a point gathering instrument with a fiber optic shape sensor, thus eliminating or minimizing disruptions in the surgical environment. Other registration techniques may be used to register a set of measured points to a pre-operative model or a model obtained using another modality. In the embodiments described below. EM sensors on the patient and the instrument and optical tracking systems for the instrument may be eliminated.

FIGS. 5A, 5B, and 5C illustrate some of the steps of the general method 450 illustrated in FIG. 4. FIG. 5A illustrates a segmented model 502 of a set of anatomic passageways created from pre-operative or intra-operative imaging data. In this embodiment, the passageways are airways of a human lung. Due to naturally occurring limitations or to limitations set by an operator, the segmented model 502 may not include all of the passageways present within the human lungs. For example, relatively narrow and/or distal passageways of the lungs may not be fully included in the segmented model 502. The segment model 502 may be a three-dimensional model, such as a mesh model, that including the walls defining the interior lumens or passageways of the lungs.

Based on the segmented model 502, a centerline segmented model 504 may be generated as shown in FIG. 5B. The centerline segmented model 504 may include a set of three-dimensional straight lines or a set of curved lines that correspond to the approximate center of the passageways contained in the segmented model 502. The higher the resolution of the model, the more accurately the set of straight or curved lines will correspond to the center of the passageways. Representing the lungs with the centerline segmented model 504 may provide a smaller set of data that is more efficiently processed by one or more processors or processing cores than the data set of the segmented model 502, which represents the walls of the passageways. In this way the functioning of the control system 112 may be improved. As shown in FIG. 5B, the centerline segmented model 504 includes several branch points, some of which are highlighted for visibility in FIG. 5B. The branch points A, B, C, D, and E are shown at each of several of the branch points. The branch point A may represent the point in the model at which the trachea divides into the left and right principal bronchi. The right principal bronchus may be identified in the centerline segment model 504 as being located between branch points A and B. Similarly, secondary bronchi are identified by the branch points B and C and between the branch points B and E. Another generation may be defined between branch points C and D. Each of these generations may be associated with a representation of the diameter of the lumen of the corresponding passageway. In some embodiments, the centerline model 504 may include an average diameter value of each segmented generation. The average diameter value may be a patient-specific value or a more general value derived from multiple patients.

In some embodiments, the centerline segmented model 504 is represented in data as a cloud, set, or collection of points in three-dimensional space, rather than as continuous lines. FIG. 5C illustrates the centerline segmented model 504 as a set of points 506. In data, each of the points of the set of model points may include coordinates such as a set of $X_M$, $Y_M$, and $Z_M$ coordinates, or other coordinates that identify the location of each point in the three-dimensional space. In some embodiments, each of the points may include a generation identifier that identifies which passageway generation the points are associated with and/or a diameter or radius value associated with that portion of the centerline segmented model 504. In some embodiments, information describing the radius or diameter associated with a given point may be provided as part of a separate data set.

After the centerline segmented model 504 is generated and stored in data as the set of points 506 shown in FIG. 5C, the centerline segmented model 504 may be retrieved from data storage for use in an image-guided surgical procedure. In order to use the centerline segmented model 504 in the image-guided surgical procedure, the model 504 may be registered to associate the modeled passageways in the model 504 with the patient's actual anatomy as present in a surgical environment. Use of the model 504 in point set registration includes using the set of points 506 from the model 504.

FIGS. 6A and 6B illustrate an exemplary surgical environment 600 according to some embodiments, with a surgical coordinate system $X_S$, $Y_S$, $Z_S$, in which a patient P is positioned on a platform 602. The patient P may be stationary within the surgical environment in the sense that gross patient movement is limited by sedation, restraint, or other means. Cyclic anatomic motion including respiration and cardiac motion of the patient P continues. Within the surgical environment 600, a point gathering instrument 604 is coupled to an instrument carriage 606. In various embodiments, the point gathering instrument 604 may use EM sensors, shape-sensors, and/or other sensor modalities. The instrument carriage 606 is mounted to an insertion stage 608 fixed within the surgical environment 600. Alternatively, the insertion stage 608 may be movable but have a known location (e.g., via a tracking sensor or other tracking device) within the surgical coordinate system. The instrument carriage 606 may be a component of a teleoperational manipulator assembly (e.g., assembly 102) that couples to the instrument 604 to control insertion motion (i.e. motion in an $X_S$ direction) and, optionally, motion of a distal end of the instrument in multiple directions including yaw, pitch, and roll. The instrument carriage 606 or the insertion stage 608 may include servomotors (not shown) that control motion of the instrument carriage along the insertion stage.

The point gathering instrument 604 may include a flexible catheter 610 coupled to a proximal rigid instrument body 612. The rigid instrument body 612 is coupled and fixed relative to the instrument carriage 606. In the illustrated embodiment, an optical fiber shape sensor 614 is fixed at a proximal reference point 616 on the rigid instrument body 612. In this embodiment, the reference point 616 is located outside of the patient anatomic passageways, but in alternative embodiments, the reference point may travel within the patient. In an alternative embodiment, the point 616 of the sensor 614 may be movable along the body 612 but the location of the point may be known (e.g., via a tracking sensor or other tracking device). The shape sensor 614 measures a shape from the reference point 616 to another point such as the distal end 618 of the catheter 610. The point gathering instrument 604 may be substantially similar to the medical instrument system 200.

A position measuring device 620 provides information about the position of the rigid instrument body 612 as it moves on the insertion stage 608 along an insertion axis A. The position measuring device 620 may include resolvers, encoders, potentiometers, and other mechanisms that determine the rotation and orientation of the motor shafts controlling the motion of the instrument carriage 606 and consequently the motion of the rigidly attached instrument body 612. In this embodiment, the insertion stage 608 is linear, but in alternative embodiments it may be curved or have a combination of curved and linear sections. Optionally, the linear track may be collapsible as described, for example, in U.S. Provisional Patent Application No. 62/029,917 (filed Jul. 28, 2014)(disclosing "Guide Apparatus For Delivery Of A Flexible Instrument And Methods Of Use") which is incorporated by reference herein in its entirety. FIG. 6 shows the instrument body 612 and carriage 606 in a retracted position along the insertion stage 608. In this retracted position, the proximal point 616 is at a position $L_0$ on the axis A. In this position along the insertion stage 608 an Xs component of the location of the point 616 may be set to a zero or original value. With this retracted position of the instrument body 612 and carriage 606, the distal end 618 of the catheter may be positioned just inside an entry orifice of the patient P. Also in this position, the position measuring device may be set to a zero or original value (e.g. I=0). In FIG. 7, the instrument body 612 and the carriage 606 have advanced along the linear track of the insertion stage 608 and the distal end of the catheter 610 has advanced into the patient P. In this advanced position, the proximal point 616 is at a position $L_1$ on the axis A.

Embodiments of the point gathering instrument 604 may collect measured points using any number of modalities, including EM sensing and shape-sensing. As the measurement points are collected from within the passageways of a patient, the points are stored in a data storage device, such as a memory. The set of measured points may be stored in a database that includes at least some, but may include all, of the measured points obtained during the procedure or immediately before the procedure. As stored in memory, each of the points may be represented by data comprising coordinates of the point, a timestamp, and a relative sensor position or individual sensor ID (when multiple sensors distributed along a length of the point gathering instrument 604 are used to determine the location of several points simultaneously). In some embodiments, data representing each point may also include a respiratory phase marker that indicates the respiratory phase of the patient in which the point was collected.

FIG. 8 is a flowchart illustrating a method 500 used to provide guidance to a clinician in an image-guided surgical procedure on the patient P in the surgical environment 600, according to an embodiment of the present disclosure. The method 500 is illustrated in FIG. 8 as a set of blocks, steps, operations, or processes. Not all of the illustrated, enumerated operations may be performed in all embodiments of the method 500. Additionally, some additional operations that are not expressly illustrated in FIG. 8 may be included before, after, in between, or as part of the enumerated processes. Some embodiments of the method 500 include instructions corresponded to the processes of the method 500 as stored in a memory. These instructions may be executed by a processor like a processor of the control system 112.

Thus, some embodiments of the method 500 may begin at a process 502, in which a calibration procedure is performed to calibrate, with a position measuring device like the point gathering instrument 604 or another suitable device, a relative position and/or orientation of a sensor reference point along an insertion path. For example, the point gathering instrument 604 of FIGS. 6 and 7 may be used to determine a position and orientation of the point 616 as the carriage 606 moves from a retracted position with the point 616 at location $L_0$ to an advanced position with the point 616 at the location $L_1$. The calibration procedure determines the direction of the movement of the point 616 for each change in the position measuring device 620. In this embodiment, where the insertion stage 608 restricts movement of the carriage 606 to a linear path, the calibration procedure determines the direction of the straight line. One such calibration method is to measure the difference in position between two points along the straight section of the catheter, the direction of that difference vector is the direction of the insertion axis. An alternative method is to constrain a known point of the catheter (e.g. the tip) in a fixed location and to measure the relative position of point 616 with respect to that known fixed point as the backend traverses along the insertion axis, and then to fit a direction vector to this collection of measured points. From the slope of the insertion stage track, the position and orientation of the point 616 in the surgical environment 600 may be determined for every corresponding measurement of the position measuring device 620. In an alternative embodiment, if the insertion stage has a curved or otherwise non-linear shape, the calibration procedure may determine the non-linear shape so that for every measurement of the position device, the position and orientation of the point 616 in the surgical environment may be determined. For example, the distal tip of the catheter may be held in a fixed position while the instrument body is routed along the non-linear insertion stage. The position and orientation data collected by the shape sensor from the fixed point 616 is correlated with the position measuring device data as the instrument body is routed along the insertion stage, thus calibrating movement of the point 616 along the axis A of the insertion stage 608.

At a process 504, the distal end 618 of the catheter traverses the patient P's anatomical passageways (e.g., airways of the patient's lungs) recording, via data from the shape sensor 614, location data for the distal end of the catheter and/or other points along the shape of the shape sensor. This location data may include, or be processed to obtain, a set of measured points as described herein. More specifically, the movement of the distal tip of the catheter 610 is controlled via teleoperational, manual, or automated control (e.g., via master assembly 106) to survey a portion of the anatomical passageways. For example, teleoperational control signals may cause the carriage 606 to move along the axis A, causing the distal tip 618 of the catheter to advance or retract within the anatomical passageways. Also or alternatively, teleoperational control signals may cause actuation of control members extending within the surgical instrument to move the distal tip 618 in a range of movements including yaw, pitch, and roll. As the catheter is moved within the plurality of passageways, shape sensor data is gathered for multiple locations of the distal tip. In some embodiments, the catheter may extend up to approximately three inches into the various passageways. In some embodiments, the catheter may be extended through or into approximately three branched generations on each side of the lung. The number of generations accessible with the catheter 610 may increase as the diameter of the flexible catheter 610 decreases and/or the flexibility of the flexible catheter increases.

With reference to FIG. 9, shape sensor data is gathered for a set of measured data points D. The measured data points may be store in memory as data sets or point pools with coordinates, timestamps, sensor IDs, respiration phase information, or the like for each gathered point. This collected set of spatial information provided by data points D from the shape sensor or other point collection device may be gathered as the distal end 618 of the catheter 610 is moved to a plurality of locations within the surgical space 600 (i.e., the teleoperational manipulator space). The location of a given collected data point $D_X$ in the surgical environment space 600 is determined by combining information from the position measuring device 620 when the distal end of the catheter is located at the point $D_X$ with the shape data from the shape sensor when the distal end of the catheter is located at the point $D_X$. Points may also be collected along the length of the catheter. In both cases, the data from the position measuring device 620 and the calibrated path of the fixed sensor point 616 provides the position of the sensor point 616 in the patient surgical environment 600 when the distal end 618 of the catheter is at the point $D_X$. For example, encoder data from one or more motors controlling movement of the carriage 606 along the track 608 and the calibration data from the movement of the carriage along the track provides the position of the sensor point 616 in the surgical environment 600 when the distal end of the catheter is at the point $D_X$. The shape sensor provides the shape of the instrument between the fixed sensor point 616 and the distal end 618. Thus, the location of the point $D_X$ (where the distal end 618 is located) in the surgical environment space 600 can be determined from the calibrated position measuring data and the shape sensor data recorded when the distal end is at point $D_X$. The location in the surgical environment 600 coordinate space for all of the data points D in the set of gathered data points (i.e. calibrated position of the proximal point 616 together combined with the shape sensor data for the location of the distal end 618 relative to the point 616) is a reference set of spatial information for the instrument that can be registered with anatomic model information.

Referring again to FIG. 8, at a process 506, one or more of the gathered data points D may correspond to landmark locations in the patient anatomy. In some embodiments, the gathered data points D that correspond to landmarks may be used to seed a registration process, such as an ICP process. This subset of gathered data points D that correspond to one or more landmarks may be referred to as seed points. The data representing the subset of gathered data points D that correspond to landmarks may include a landmark indicator when stored in memory. With reference to FIG. 11, a set of anatomical passageways 700 include main carinas C1, C2, C3 where the passageways 700 fork. A data point D can be gathered for the location of each carina by moving the distal end of the catheter to the respective carina locations. For example, a data point $D_{L1}$ can be gathered at the carina $C_1$. A data point $D_{L2}$ can be gathered at the carina $C_2$. A data point $D_{L3}$ can be gathered at the carina $C_3$. The carinas or other suitable landmarks can be located in the patient surgical environment 600 as described above for point $D_X$. The process 506 is optional and may be omitted if alternative seeding techniques are used.

Referring again to FIG. 8, at a process 508 anatomical model information is received. The anatomic model information may be the segmented centerline model 504 as described in FIG. 5C. Referring again to FIG. 9, the anatomical model information may be represented as a centerline model 550 of branched anatomic passageways. In some embodiments, the model may include one or more landmark points to match to the seed points $D_{L1}$, $D_{L2}$, and $D_{L3}$. These points included in the model to match to the seed points $D_{L1}$, $D_{L2}$ and $D_{L3}$ may not be centerline points in some embodiments, but may be included in the centerline model 550 to facilitate seeding of a subsequent registration process. In some embodiments, the centerline model 550 may include more model landmark points than $M_{L1}$, $M_{L2}$, and $M_{L3}$.

Referring again to FIG. 8, at a process 510 registration of the anatomical model information 550 with the set of gathered data points D from the surgical environment 600 is performed. Registration may be accomplished using a point set registration algorithm such as an iterative cloud point (ICP) technique as described in processes 512-520, or by implementation of another registration algorithm. At process 512, the ICP registration is seeded with known information about the displacement and orientation relationship between the patient surgical environment and the anatomical model. In this embodiment (FIG. 11), for example, the carina landmarks $C_1$, $C_2$, $C_3$ are identified in the anatomical model information as points $M_{L1}$, $M_{L2}$, $M_{L3}$. In alternative embodiments, the anatomical model information may be represented in other ways, e.g. as centerline segments or axes of a 3D mesh model. Or alternatively, the model may be expressed as a volume constructed from 3D shapes such as cylinders or as a 3D image. The recorded landmark data points $D_{L1}$, $D_{L2}$, $D_{L3}$ from the patient surgical environment are each matched to a corresponding model points $M_{L1}$, $M_{L2}$, $M_{L3}$, (i.e., $D_{L1}$ matches to $M_{L1}$, etc.) With the points matched, an initial transform (e.g., change in position and/or orientation) between landmark data points $D_{L1}$, $D_{L2}$, $D_{L3}$ and model points $M_{L1}$, $M_{L2}$, $M_{L3}$ is determined. The transform may be a rigid transform in which all landmark data points are transformed by the same change in position and orientation or may be a non-rigid transform in which the landmark datapoints are transformed by different changes in position and orientation. The transform determined with the landmark data points $D_{L1}$, $D_{L2}$, $D_{L3}$ may applied to all of the gathered data points D. This seeding process, based on a few landmark points, provides an initial coarse registration of the gathered data points D to the anatomical model.

An alternative method to obtain an initial coarse registration is to use approximately known information about the teleoperational manipulator assembly and the patient location. The teleoperational manipulator assembly may be instrumented with encoders or other sensors that measure the relative pose of the insertion track with respect to gravity. This information may be combined with patient orientation assumptions, e.g., the patient is lying on his back, and the assumption that the insertion track is placed at the patient's mouth. The combined information may thus also provide an approximate relative orientation and position of the instrument with respect to the patient and be sufficient as seeding registration to proceed with full registration.

At a process 514, with the initial coarse registration performed, the set of gathered data points D is matched to the anatomical model information 550 (FIG. 9). In this embodiment, the anatomical model information is a set of points along the centerlines of the anatomic model. The ICP algorithm identifies matches between closest points in the gathered data points D and in the set of anatomic model points. In various alternatives, matching may be accomplished by using brute force techniques, KD tree techniques, maximum distance threshold calculations, maximum angle threshold calculations, model centerline points, model mesh points, and/or model volume points. In another embodiment, matching is not required at all, but rather each gathered point is mapped to a nearest point on or within the model using some explicit mapping function or by using a look-up-table. The matching or mapping between gathered points and model points may further be informed by additional criteria such as the insertion depth, respiratory phase, motor torque, velocity, etc.

At a process 516, the motion needed to move the set of gathered data points D to the position and orientation of the matched anatomic model points is determined. More specifically, an overall offset in position and orientation is determined for the set of gathered data points D. FIG. 9, for example, illustrates an initial offset of approximately 20° in orientation and 40 mm in displacement between the gathered data points D and the anatomical model information 550.

At a process 518, the set of gathered data points D are transformed using a rigid or non-rigid transformation that applies the computed offset in displacement and orientation to move each point in the set of gathered data points D. As shown in FIG. 10, the set of gathered data points D is transformed to converge with the model points 550.

At a process 520, the convergence of the gathered data points D and the matched anatomic model points 550 are evaluated. In other words, error factors for orientation and displacement may be determined for each matched point set. If the error factors in aggregate are greater than a threshold value, additional iterations of processes 514-520 may be repeated until the overall position and orientation error factors falls below the threshold value.

The registration process 510 may recomputed multiple times during a surgical procedure (e.g. approximately twice per hour, but may be more or less frequently) in response to deformation of the passageways caused by cyclic anatomical motion, instrument forces, or other changes in the patient environment.

After the anatomic model and the patient environment are registered, an image guided surgical procedure may, optionally, be performed. Referring again to FIG. 8, at process 522, during a surgical procedure, a current location of a surgical instrument in the surgical environment is determined. More specifically, the data from the position measuring device 620 and the calibrated path of the fixed sensor point 616 provides the position of the sensor point 616 in the patient surgical environment 600 when the catheter is in a current location. The shape sensor provides the shape of the instrument between the fixed sensor point 616 and the distal end 618. Thus, the current location of the catheter 210 and particularly the distal end 618 of the catheter in the surgical environment space 600 can be determined from the calibrated position measuring data and the shape sensor data.

At process 524, the previously determined registration transforms are applied to the current instrument position and shape data to localize the current instrument to the anatomic model. For example, the current position and orientation for the distal end of the instrument, data point $D_{current}$ is transformed using the one or more transform iterations determined at process 510. Thus, the data point $D_{current}$ in the surgical environment 600 is transformed to the anatomic model space. In an alternative embodiment, the anatomical model may instead be registered to the surgical environment in which the catheter position data is gathered.

At process 526, optionally, the localized instrument may be displayed with the anatomic model to assist the clinician in an image guided surgery. FIG. 12 illustrates a display system 800 displaying a rendering of anatomical passageways 802 of a human lung 804 based upon anatomical model information. With the surgical environment space registered to the model space as described above in FIG. 8, the current shape of the catheter 610 and the location of the distal end 618 may be located and displayed concurrently with the rendering of the passageways 802.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
 a manipulator configured to move a medical instrument in a medical environment; and
 a processing unit operatively coupled to the manipulator, wherein the processing unit is configured to:
  receive, from a position sensor system, a collected set of spatial information for a distal portion of the medical instrument, the collected set of spatial information collected at a plurality of locations within a set of anatomic passageways, wherein the collected set of spatial information is measured as a rigid instrument body disposed at a proximal portion of the medical instrument is moved in an insertion or retraction direction by the manipulator;
  receive, from a position measuring device of the manipulator, a set of position information related to a position of the rigid instrument body when the distal portion of the medical instrument is at each of the plurality of locations as the medical instrument is moved in the insertion or retraction direction, wherein the set of position information is in an environment coordinate space;
  based at least in part on the set of position information, determine a subset of the collected set of spatial information for the distal portion of the medical instrument relative to the environment coordinate space; and
  based on the subset of the collected set of spatial information, determine an initial transform for registering the collected set of spatial information with a set of anatomical model information in a model coordinate space.

2. The system of claim 1, wherein the manipulator comprises an instrument carriage couplable to the rigid instrument body of the medical instrument to control movement of the medical instrument in the insertion or retraction direction.

3. The system of claim 2, wherein the position measuring device is configured to determine an orientation of at least one motor shaft controlling motion of the instrument carriage.

4. The system of claim 1, wherein the position measuring device comprises at least one of a motor position sensor, a resolver, an encoder, or a potentiometer.

5. The system of claim 1 wherein the position sensor system comprises a fiber optic shape sensor extending between the distal portion of the medical instrument and the rigid instrument body.

6. The system of claim 5 wherein the fiber optic shape sensor is fixed at the rigid instrument body.

7. The system of claim 1 wherein the position sensor system comprises at least one electromagnetic sensor disposed in the distal portion of the medical instrument.

8. The system of claim 1 wherein the processing unit is further configured to receive commands from a control device to move the medical instrument through the plurality of locations within the set of anatomic passageways.

9. The system of claim 1 wherein the set of anatomical model information is generated from a set of pre-operative anatomic images.

10. The system of claim 1 wherein the processing unit is configured to:
 register the collected set of spatial information with the set of anatomical model information.

11. The system of claim 10 wherein registering the collected set of spatial information with the set of anatomical model information includes applying the initial transform to the collected set of spatial information.

12. The system of claim 1, wherein the subset of the collected set of spatial information for the distal portion of the medical instrument includes at least one data point corresponding to a main carina of the set of anatomic passageways.

13. A system comprising:
 an instrument comprising:
 a rigid instrument body;
 a flexible catheter extending from the rigid instrument body; and
 a position sensor system configured to collect a collected set of spatial information for a distal portion of the flexible catheter at a plurality of locations within a set of anatomic passageways;
 a manipulator comprising:
  an instrument carriage configured to receive the rigid instrument body and move the rigid instrument body in a medical environment; and
  a position measuring device configured to determine a set of position information for the instrument carriage in an environment coordinate space as the rigid instrument body is moved in an insertion or retraction direction; and
 a processing unit operatively coupled to the manipulator and configured to:
  receive the collected set of spatial information;
  receive the set of position information;
  based at least in part on the set of position information, determine a subset of the collected set of spatial information; and based on the subset of the collected set of spatial information, determine an initial transform for registering the collected set of spatial information with a set of anatomical model information in a model coordinate space.

14. The system of claim 13, wherein the position measuring device is configured to determine an orientation of at least one motor shaft controlling motion of the instrument carriage.

15. The system of claim 13, wherein the position measuring device comprises at least one of a motor position sensor, a resolver, an encoder, or a potentiometer.

16. The system of claim 13 wherein the position sensor system comprises a fiber optic shape sensor extending between the distal portion of the flexible catheter and the rigid instrument body.

17. The system of claim 13 wherein the position sensor system comprises at least one electromagnetic sensor disposed in the distal portion of the flexible catheter.

18. The system of claim 13 wherein the processing unit is further configured to receive commands from a control device to move the instrument through the plurality of locations within the set of anatomic passageways.

19. The system of claim 13 wherein the processing unit is configured to:
   register the collected set of spatial information with the set of anatomical model information.

20. The system of claim 19 wherein registering the collected set of spatial information with the set of anatomical model information includes applying the initial transform to the collected set of spatial information.

* * * * *